US010632172B2

(12) United States Patent
Kumar et al.

(10) Patent No.: US 10,632,172 B2
(45) Date of Patent: Apr. 28, 2020

(54) INJECTABLE SELF-ASSEMBLING ANTIBACTERIAL PEPTIDE HYDROGELS

(71) Applicant: New Jersey Institute of Technology, Newark, NJ (US)

(72) Inventors: Vivek A. Kumar, Newark, NJ (US); Peter Nguyen, New Rochelle, NY (US); Biplab Sarkar, Newark, NJ (US); Shivani Jaisinghani, Morganville, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 0 days.

(21) Appl. No.: 16/438,872

(22) Filed: Jun. 12, 2019

(65) Prior Publication Data

US 2020/0000875 A1 Jan. 2, 2020

Related U.S. Application Data

(60) Provisional application No. 62/685,616, filed on Jun. 15, 2018.

(51) Int. Cl.
*A61K 38/16* (2006.01)
*A61L 31/14* (2006.01)
*A61L 27/52* (2006.01)
*A61K 9/70* (2006.01)
*A61K 9/00* (2006.01)
*A61L 27/22* (2006.01)

(52) U.S. Cl.
CPC .......... *A61K 38/164* (2013.01); *A61K 9/0014* (2013.01); *A61K 9/0019* (2013.01); *A61K 9/70* (2013.01); *A61L 27/22* (2013.01); *A61L 27/52* (2013.01); *A61L 31/145* (2013.01); *A61L 2400/06* (2013.01)

(58) Field of Classification Search
None
See application file for complete search history.

(56) References Cited

U.S. PATENT DOCUMENTS 9,526,762 B1 12/2016 Hartgerink et al.

OTHER PUBLICATIONS

American Diabetes Association, Statistics about Diabetes , Web, Accessed Oct. 9, 2016 <http://www.diabetes.org/diabetes-basics/statistics/>.
Aulisa et al., Self-Assembly of Multidomain Peptides: Sequence Variation Allows Control Over Cross-Linking and Viscoelasticity, Biomacromolecules, Aug. 2009, vol. 10, pp. 2694-2698.
Baek, et al., The Tetrapeptide Arg-Leu-Tyr-Glu Inhibits VEGF-Induced Angiogenesis, Biochemical and Biophysical Research Communications., Available online Jun. 2015, pp. 532-537, vol. 463.
Breij et al., The Antimicrobial Peptide SAAP-148 Combats Drug-Resistant Bacteria and Biofilms, Science Translational Medicine, vol. 10, EAAN4044, Mar. 2018, pp. 1-14.
Bryers, James D., Medical Biofilms, Biotechnology and Bioengineering,vol. 100, No. 1, May 2008, pp. 1-31.
Davidson et al., Kringle 5 of Human Plasminogen Induces Apoptosis of Endothelial and Tumor Cells through Surface-Expressed Glucose-Regulated Protein 78, Cancer Research, Jun. 2005, pp. 4663-4672, vol. 65, No. 11.
Dong et al., Self-Assembly of Multidomain Peptides: Balancing Molecular Frustration Controls Conformation and Nanostructure, Journal of the American Chemical Society, Sep. 2007, vol. 129, pp. 12468-12472.
Glukhov, et al., Basis for Selectivity of Cationic Antimicrobial Peptides for Bacterial Versus Mammalian Membranes*, The Journal of Biological Chemistry, vol. 280, No. 40, Oct. 2005, pp. 33960-33967.
Kumar et al., Drug-Triggered and Cross-Linked Self-Assembling Nanofibrous Hydrogels, Journal of the American Chemical Society, vol. 137, Apr. 2015, pp. 4823-4830.
Kumar et al., Highly angiogenic peptide nanofibers, ACS Nano, Published online Jan. 2015, pp. 860-868, vol. 9, No. 1, American Chemical Society.
Kumar et al., Self-Assembling Multidomain Peptides Tailor Biological Responses Through Biphasic Release, Biomaterials, vol. 52, Jun. 2015, pp. 71-78.
Kumar et al., Treatment of hind limb ischemia using angiogenic peptide nanofibers, Biomaterials, Available online Apr. 2016, pp. 113-119, vol. 98.
Liu et al., Self-Assembled Cationic Peptide Nanoparticles as an Efficient Antimicrobial Agent, Nature Nanotechnology, vol. 4, Jul. 2009, pp. 457-463.
Mayo Clinic Staff, Lasik Eye Surgery Risks, Web, Accessed Feb. 19, 2017, <http://www.mayoclinic.org/tests-procedures/lasik-eye-surgery/basics/risks/prc-20019041>.

(Continued)

*Primary Examiner* — Marcela M Cordero Garcia
(74) *Attorney, Agent, or Firm* — Lerner, David, Littenberg, Krumholz & Mentlik, LLP

(57) ABSTRACT

A set of cationic amphiphilic self-assembled peptides (CASPs) is presented that employ high-charge density at fiber edges to disrupt bacterial membranes. CASP nanofibers are effective against *Pseudomonas* biofilms. There is an inherent trade-off between the ability of the peptides to undergo nanofibrous self-assembly and having a high terminal charge density required for effective bactericidal efficacy. The self-assembled peptide hydrogel presented achieves a balance of these opposing factors. Also demonstrated is the applicability of the new composition in an injectable hydrogel formulation. A CASP platform may be useful for topical application and integration into medical coatings, grafts, devices, and prostheses, thereby reducing risk of bacterial infection and related failure.

17 Claims, 11 Drawing Sheets
(11 of 11 Drawing Sheet(s) Filed in Color)
Specification includes a Sequence Listing.

(56) References Cited

OTHER PUBLICATIONS

Meads et al., What is the cost of blindness, The British Journal of Ophthalmology, Sep. 2003, pp. 1201-1204, vol. 87.

Nguyen et al., Kringle 5 of Human Plasminogen, an Angiogenesis Inhibitor, Induces Both Autophagy and Apoptotic Death in Endothelial Cells, Blood, Jun. 2007, pp. 4793-4802, vol. 109, No. 11, The American Society of Hematology.

Nguyen et al., Self Assembly of an Anti-Angiogenic Nanofibrous Peptide Hydrogel, ACS Appl. Bio Mater., Aug. 2018, pp. 865-870, vol. 1.

Sarkar et al., Self-Assembly of Fiber-Forming Collagen Mimetic Peptides Controlled by Triple-Helical Nucleation, Journal of the American Chemical Society, vol. 136, Oct. 2014, pp. 14417-14424.

Wang et al., Inhibition of Pathological Corneal Neovascularization by a Small Peptide Derived from Human Apolipoprotein (a) Kringle V, Cornea, Apr. 2014, pp. 405-413, vol. 33, No. 4.

Yu et al., Antiangiogenic Therapy with Human Apolipoprotein(a) Kringle V and Paclitaxel in a Human Ovarian Cancer Mouse Model, Translational Oncology, Jun. 2014, pp. 368-376, vol. 7, No. 3.

Zhang, et al., Plasminogen Kringle 5 Reduces Vascular Leakage in the Retina in Rat Models of Oxygen-Induced Retinopathy and Diabetes, Diabetologia, Published online Dec. 2003, pp. 124-131, vol. 47.

Zhang, et al., Systemic and Periocular Deliveries of Plasminogen Kringle 5 Reduce Vascular Leakage in Rat Models of Oxygen-Induced Retinopathy and Diabetes, Current Eye Research, 2005, pp. 681-689, vol. 30, No. 8.

Rational Design Considerations

| | CASP-K2 | CASP-K4 | CASP-K6 | CASP-K8 |
|---|---|---|---|---|
| # of charged residues (C): | 4 | 8 | 12 | 16 |
| # of neutral residues (N): | 12 | 12 | 12 | 12 |
| C/N: | 1/3 | 2/3 | 1 | 4/3 |
| antibacterial efficacy: | →→→→→→→→→→→→→→→→→→→→→→→→→→→→→ | | | |
| nanofibrillar propensity: | ←←←←←←←←←←←←←←←←←←←←←←←←←←←←← | | | |

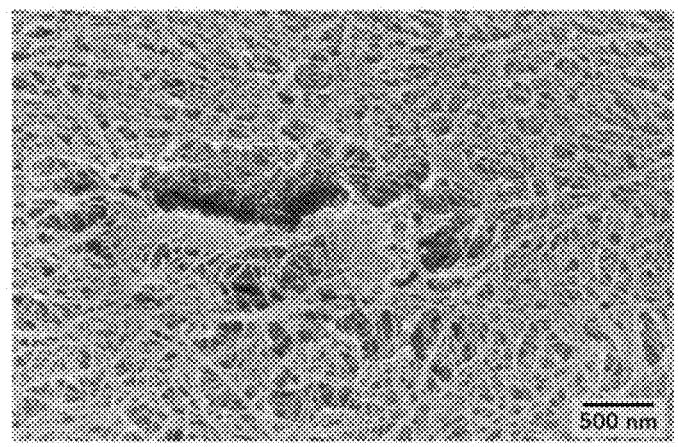
FIGURE 14
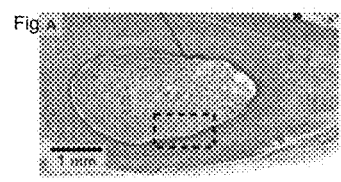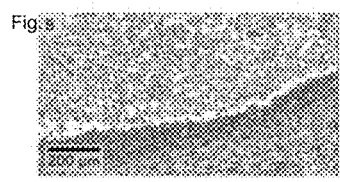
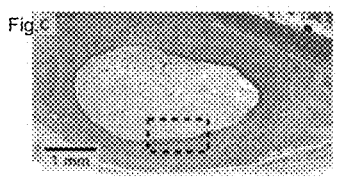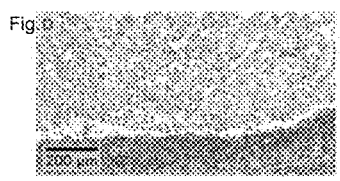
FIGURES 15A-15D

INJECTABLE SELF-ASSEMBLING ANTIBACTERIAL PEPTIDE HYDROGELS

CROSS-REFERENCE TO RELATED APPLICATIONS

The present application claims the benefit of the filing date of U.S. Provisional Patent Application No. 62/685,616 filed on Jun. 15, 2018 the disclosure of which is hereby incorporated herein by reference.

FIELD OF USE

The present application discloses a self-assembled nanofiber platform capable of disrupting bacterial colonies in stationary biofilms. More particularly, the present application relates to a self-assembled antibacterial system that may be applied as a topical antibiotic and also may be incorporated into existing medical grafts, devices, and prostheses.

BACKGROUND OF THE INVENTION

Infectious contamination in the health care setting is a growing concern in modern times. The three bacteria most commonly found in a hospital setting include two organisms that are resistant to antibiotics. Surfaces on for example medical instruments, trays, and other holding or supply areas in the healthcare environment serve as reservoirs for microorganisms that can cause infection in patients and healthcare workers due to cross contamination. Since modern-day patient care is administered in a variety of clinical environments, there is concern about the contamination risks across the entire healthcare network, including hospitals, ambulatory care practices, surgery centers, primary care and other outpatient offices.

Bacterial contamination and colonization of medical devices and prostheses cause significant morbidity and mortality worldwide. The first line of defense against such bacterial threats is physiologic antimicrobial peptides (AMPs). Substances such as cationic amphiphilic self-assembled peptides (CASPs) employ high-charge density to disrupt bacterial membranes. CASP nanofibers are shown to be effective against *Pseudomonas aeruginosa* colonies that are a major cause of bacterial infections. However, there is an inherent trade-off between the nanofibrous self-assembly and bactericidal efficacy for these peptides.

Furthermore, bacterial biofilm formation on medical devices can cause severe infections. Such infections pose a major problem for implanted devices and prostheses such as vascular grafts. As tissue-engineered scaffolds become vital solutions for tissue repair and regeneration, bacterial infection of such constructs become a significant issue.

Therefore, there exists a critical need for a self-assembled antibacterial system that can be applied as a topical antibiotic and incorporated into existing medical devices such as grafts, prostheses and the like. There is also a need for a composition that achieves a beneficial balance between the usefulness of a nanofibrous self-assembly peptide and the undesirable results on bactericidal efficacy.

SUMMARY OF THE INVENTION

The hydrogel disclosed aims to cure bacterial infections by inhibiting the growth of bacterial biofilms. The presently disclosed composition and method solves the problems of current state of the art and provides many more benefits. The present solution integrates antimicrobial domains to self-assembling nanofibers and overcomes major problems with formulation, drug delivery, and in vivo persistence. As shown herein, a set of cationic amphiphilic self-assembled peptides (CASPs) are designed that employ high-charge density to disrupt bacterial membranes. The compositions are readily injectable, persist in vivo, and sustain localized efficacy for prolonged periods. The composition and method of the present invention utilizes a self-assembling peptide that is dissolved in buffer and forms an antibacterial hydrogel. The CASP platform may be useful for topical application and integration into medical coatings, grafts, devices, and prostheses, reducing risk of bacterial infection and related failure. For example, a CASP hydrogel may be topically applied or integrated into a wound bed directly, or integrated into medical coatings, grafts, devices, and prostheses for reducing risk of bacterial infection and related failure.

The composition may also treat localized infections, and may be used to prevent bacterial growth or infection. The composition may also be used in conjugation with other biomaterials, and used to modify existing biomaterials. Benefits can be seen in uses in both infectious disease (local, topical), and systemic administration. Benefits are also envisioned in use in the surgical field for local topical delivery.

The proposed set of cationic amphiphilic self-assembling peptides (CASPs) is based on nanofibrous multidomain peptides. The central domain of all CASPs comprises in one embodiment of alternating serines and leucines, whereas the flanking domains are composed of a series of lysine residues. The length of the terminal charged domain varies among CASPs. Higher positive charge correlate with more robust antibacterial activity since the highly cationic peptides would be able to attach to a negatively charged bacterial cell membrane more effectively.

One object of the invention is to devise a self-assembling peptide, CASP-K6, that is optimized for both fibrillar self-assembly and antibacterial efficacy. Self-assembled nanostructures have higher antimicrobial efficacy compared to the corresponding unassembled peptide. This higher antimicrobial effect is due to a higher local density of functional bactericidal domains in the self-assembled nanostructure. Variations of this antibacterial Multidomain Peptide (MDP) include, but are not limited to, the MDP sequence containing three described domains: the termini (charged amino acid residues), the midblock (alternating hydrophobic and hydrophilic residues) and the signaling domain that may be altered.

Hydrogelation of the CASP system may be useful for topical applications on infected wounds, similar to previous applications of self-assembling peptides for rapid hemostasis and wound healing. The anti-bacterial hydrogel has the CASP, preferably CASP-K6, intrinsically undergo self-hydrogelation in aqueous solutions without addition of an exogenous gel base. Comparable antibacterial peptides are often mixed with a gel base (such as hypromellose) to obtain a viscoelastic hydrogel formulation. The supramolecular design of the peptide allows formation of an antibacterial hydrogel at physiological pH and ionic strength, without the addition of a gel base. Rheometry suggests that the CASP-K6 hydrogel has a storage modulus >100 Pa, comparable to previous self-assembled therapeutic peptide hydrogels that are significantly less in storage modulus. Fibrillar assembly of CASP-K6 is facilitated by non-covalent crosslinking of the nanofibers by polyvalent anions. Thus, the hydrogel may liquefy under high shear strain, as well as rapidly recover its viscoelasticity ($G'/G''$) when the force is removed. The shear-thinning and rapid recovery of the hydrogel allows the gel to be syringe aspirated and injected into infection sites in vivo.

The above objects and advantages are met by the present invention. In addition the above and yet other objects and advantages of the present invention will become apparent from the hereinafter-set forth Brief Description of the Drawings, Detailed Description of the Invention, and claims appended herewith. These features and other features are described and shown in the following drawings and detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

So that those having ordinary skill in the art will have a better understanding of how to make and use the disclosed composition and methods, reference is made to the accompanying figures wherein:

FIG. 2A illustrates the peptides have a central domain consisting of alternating hydrophilic (serine, shown in green) and hydrophobic (leucine, shown in red) residues; there are positively charged domains (lysine residues, shown in blue) of varying length at the termini; FIG. 2B shows that fibrillar self-assembly is driven by shielding of hydrophobic residues at the core of the nanofiber as well as the formation of canonical β-sheet hydrogen bonds, however, the supramolecular polymerization is opposed by electrostatic repulsion among the charged terminal domains, this supramolecular frustration[1] determines the dynamic equilibria among the monomers and multimers;

FIG. 3A shows the mass of CASP-K2 is 1773 Da., the observed peak in MALDI-MS is at 1773 Da.; FIG. 3B shows the mass of CASP-K4 is 2286 Da., the observed peaks in ESI-MS are at 2287 Da and at 1144 Da (M/2 peak); FIG. 3C shows the expected mass of CASP-K6 is 2799 Da., the observed peaks in ESI-MS are at 1400 Da (M/2 peak) and at 560 Da (M/5 peak); and FIG. 3D shows the expected mass of CASP-K8 is 3311 Da., the observed peaks in MALDI-MS are at 3311 Da, 3369 Da (monoacetate), 3430 Da (diacetate), and 3487 Da (triacetate);

FIG. 4A shows a photograph of formulations used for each of the CASPs, CASP-K2 through CASP-K6 formed hydrogels while CASP-K8 failed to form a gel; FIG. 4B is a CD spectra of CASPs (0.002% solution), CASP-K2 through CASP-K6 formed β-sheets (characteristic minimum at ~216 nm), but CASP-K8 remained in a random-coil secondary conformation (characteristic minimum at 197 nm), molar residual ellipticity (MRE) was calculated from measured ellipticity;

FIG. 5A is a photomicrograph showing critical-point-dried hydrogel samples were sputter-coated with gold/palladium and imaged with SEM, revealing the fibrous mesh-like underlying architecture of the assembly; FIG. 5B is a photomicrograph showing AFM on a diluted peptide hydrogel confirmed the dimensions of the nanofibers (height=~2 nm, width=~11 nm); FIG. 5C is a graph showing at low shear strain (e.g., at 1% strain), CASP-K6 formed a viscoelastic hydrogel (G'=~210 Pa), at high shear strain (>30% strain), the gel liquefied (G'<G"); and FIG. 5D is a graph showing when repeated strain cycles (1% and 100% strain) were applied, the viscoelastic hydrogel underwent liquefaction (at high shear) and promptly recovered G' when the strain was lowered, repeated strain cycles demonstrated hydrogel resilience;

FIGS. 9A-9B are photographs of *Pseudomonas aeruginosa* PAO1 colonies grown on an agar plate, the rod-shaped cells can be identified by SEM at different resolutions (false colored in panel shown in FIG. 9B); FIG. 9C is a photograph illustrating treatment with CASPs disrupted the bacterial colonies; FIG. 9D is a graph showing the analysis of multiple panels, such as C, showed that CASP-K6 and CASP-K8 were very effective in disrupting the bacterial layer (distinct Greek letters denote significant differences); and FIG. 9E is an SEM image of the bacterium lysed by CASP-K6 nanofibers, where the negatively charged bacterial cell membrane associated with the cationic amphiphilic nanofibers, lysing as the osmotic homeostasis of the cell became disrupted;

FIG. 14 is a false colored image of the bacterium (in pink) entrapped and lysed by the nanofibers (in green) of CASP-K6;

FIGS. 15A-15D are images showing in vivo persistence of a CASP-K6 hydrogel implant in a rat subcutaneous pocket (dorsal aspect) after 7 days, the implant was visible at the center in FIG. 15A and FIG. 15C and at the top in FIG. 15B and FIG. 15D, the hydrogel was lightly infiltrated with cells after 7 days and was clearly visible by histology (FIGS.

15A-B: H&E staining, 2× and 10× magnification; FIGS. 15C-D: Masson's trichrome staining, 2× and 10× magnification);

FIGS. 16A, 16B,16E, and 16F: H&E staining; FIGS. 16C, 16D, 16G, and 16H: Masson's trichrome staining, 16A, 16C, 16E, and 16G: 2× magnification; 16B, 16D, 16F, and 16H: 10× magnification;

DETAILED DESCRIPTION

Figures 1, 2A, 2B:
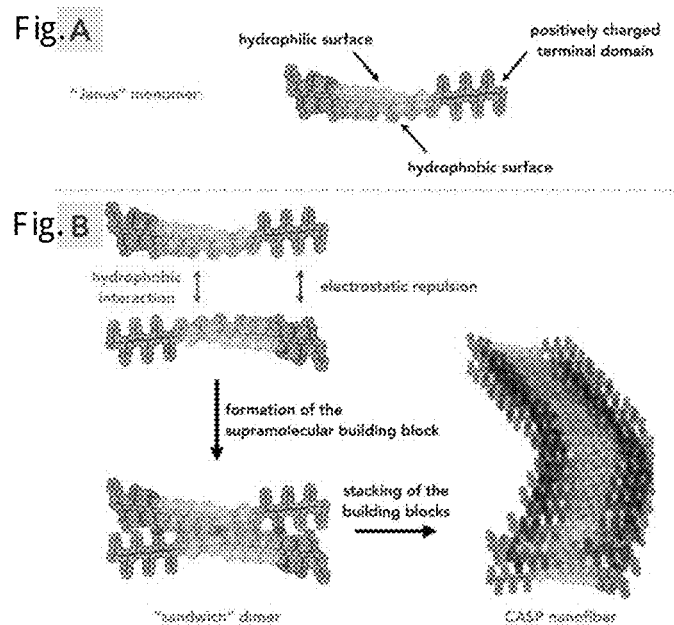
FIG. 1 is a chart showing design considerations for the CASP series, with increasing charge on the peptide monomer, the fibrillar self-assembly becomes less likely due to intra-fibrillar electrostatic repulsion, however, the antibacterial efficacy should increase simultaneously due to increased ease of attachment to negatively charged bacterial membranes.
FIG. 2A-2B is an illustration of a design and hierarchical self-assembly of the cationic nanofibrils.
Figures 3A, 3B, 3C, 3D:
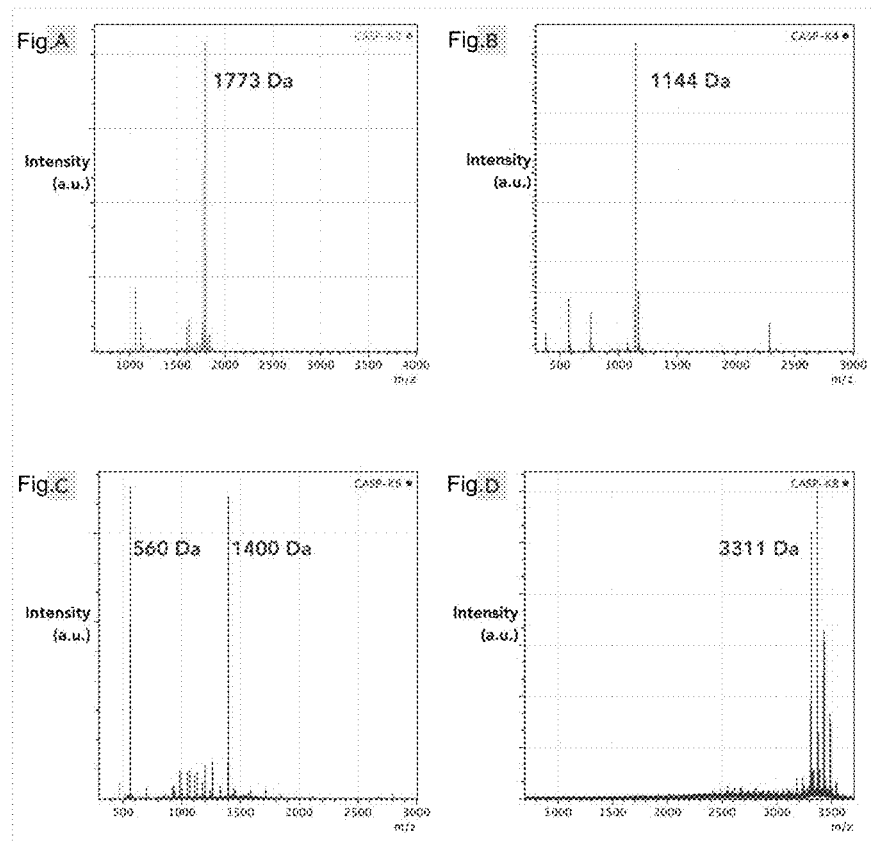
FIGS. 3A-3D are mass spectra of CASP peptides.

Shown and described are compositions and methods that comprise a self-assembling peptide that forms an antibacterial hydrogel. The CASP nanofibers self-assemble into robust hydrogels and are potent disruptors of bacterial biofilms. These hydrogels may, depending on the implementation, be syringe aspirated and injected into a target site. The self-assembly of the peptide monomers into nanofibers is promoted, among other things, by canonical beta-sheet hydrogen bonding as well as hydrophobic stabilization due to the burying of the non-polar amino acids.

Stacking of peptide monomers into a fibrillar assembly is impeded by electrostatic repulsion among positively charged residues at the termini. A supra-molecular tradeoff inherent in this scenario is responsible for the properties of the nanofibers.

A novel self-assembling peptide, CASP-K6, is devised herein that is optimized for both fibrillar self-assembly and antibacterial efficacy. Self-assembled nanostructures have been shown to have higher antimicrobial efficacy compared to the corresponding unassembled peptide, due to higher local density of functional bactericidal domains.

The fibrillar self-assembly of the peptides is driven by the tendency of the hydrophobic leucine residues shielded from the surrounding aqueous environment and the ability of the backbone amide groups to form hydrogen bonds typical of beta-sheet nanofibers. A series of CASPs are synthesized through solid phase peptide synthesis and verified by mass spectrometry.

In one example, after purification and lyophilization, the peptides are dissolved in 298 mM sucrose solution to prepare 2% (w/v) solutions. After the addition of 10×PBS (pH 7) to the peptide solution (in a 1:9 volumetric ratio), hydrogels form within seconds. Biofilms of the gram-negative bacteria *Pseudomonas putida* are grown on agar plates and CASP solutions are applied on top of established biofilms to test their ability to disrupt the bacterial colony. Cationic amphiphilic peptide nanofibers show noticeable bactericidal effect on biofilms. This effect is correlated with the terminal charge on the cationic nanofibers, consistent with initial hypothesis contained herein that higher terminal charge facilitates the association of the peptide nanofibrils with the bacterial cell membrane. The effect of the antibacterial hydrogel is localized on the biofilm.

A proposed set of cationic amphiphilic self-assembling peptides (CASPs) shown below in Table 1 is based on nanofibrous multidomain peptides (MDP). The CASP-K6 is a new composition. Other CASPs in Table 1 were previously used for a variety of tissue engineering applications, but not for the present application. All four peptides (Table 1) are combinations of just three amino acid residues: serine (hydrophilic, neutral), leucine (hydrophobic, neutral), and lysine (cationic). The amphiphilic peptides is designed with varying charge density per monomer (i.e., in a range of about +4 to about +16). The central domain of all CASPs comprises of alternating serines and leucines, whereas the flanking domains are composed of a series of lysine residues.

The length of the terminal charged domain varies among CASPs as shown in the below Table 1 and FIG. 1. It was hypothesized that a higher positive charge would correlate with more robust antibacterial activity, since the highly cationic peptides would be able to attach to negatively charged bacterial cell membrane more effectively. It is known that natural AMPs tend to be cationic.

TABLE 1

Sequences of CASPs.

| Peptide | Sequence |
| --- | --- |
| CASP-K2 | KKSLSLSLSLSLSLKK<br>SEQ. ID. NO. 1 |
| CASP-K4 | KKKKSLSLSLSLSLSLKKKK<br>SEQ. ID. NO. 2 |
| CASP-K6 | KKKKKKSLSLSLSLSLSLKKKKKK<br>SEQ. ID. NO. 3 |
| CASP-K8 | KKKKKKKKSLSLSLSLSLSLKKKKKKKK<br>SEQ. ID. NO. 4 |

In the above Table 1, positively charged amino acids (lysines) are shown as "K", hydrophilic amino acids (serines) are shown as "S", and hydrophobic residues (leucines) are shown as "L". CASP-K2 has been previously reported as a multifunctional scaffold. Depending on the embodiment, the self-assembled nanofiber platform may have the lysine (K) substituted for any positively charged amino acid. Positively charged amino acids, include, for example, the hydrogel CASP again, may have the lysine (K) substituted for a positively charged amino acid selected from a group consisting of arginine (Arg, R), histidine (His, H), modified or unnatural positively charged monovalent or polyvalent amino acids, and any combination thereof. In addition, the peptide may have any combination of K, S, and L. It is also within the scope of this disclosure that the self-assembled nanofiber platform may improve antimicrobial effects by either increasing or decreasing the number of K, S, and L amino acids in the peptide. Furthermore, the anti-bacterial hydrogel may contain a midblock amphiphilic SL (serine-lysine) repeats that promote fibrillation while lysines (L) provide solubility and anti-bacterial effect, and whose domains and number of repeats are balanced to allow solubilization and hydrogelation.

The fibrillar self-assembly of the peptides as shown in FIGS. 2A-2B is driven by the tendency of the hydrophobic residues to be shielded from the surrounding aqueous environment and the ability of the backbone amide groups to form hydrogen bonds typical of β-sheet nanofibers.

Although more charged nanofibers may have higher antibacterial activity, their fibrillar self-assembly can be inhibited by the repulsion among the terminal lysine residues as shown in FIGS. 2A-2B and FIG. 1. Optimization of this fundamental trade-off led to a lead peptide CASP-K6, which self-assembles into a nanofibrous hydrogel and retains antimicrobial efficacy.

Examples

To facilitate a better understanding of the present invention, the following examples of specific instances are given. In no way should the following examples be read to limit or define the entire scope of the invention. The following are given merely to demonstrate the principles of the invention. The following materials and methods were employed for the Example below.

In this example, a series of CASPs was explored. The series of CASPs were synthesized through solid-phase peptide synthesis and verified by mass spectrometry as shown in FIGS. 3A-3D. After purification and lyophilisation, the peptides were dissolved in 298 mM sucrose solution to prepare 2% (w/v) solutions. After the addition of 10×PBS (pH 7) to the peptide solution (in a 1:9 volumetric ratio), CASP-K2 through CASP-K6 formed hydrogels within seconds.

Figures 4A, 4B:
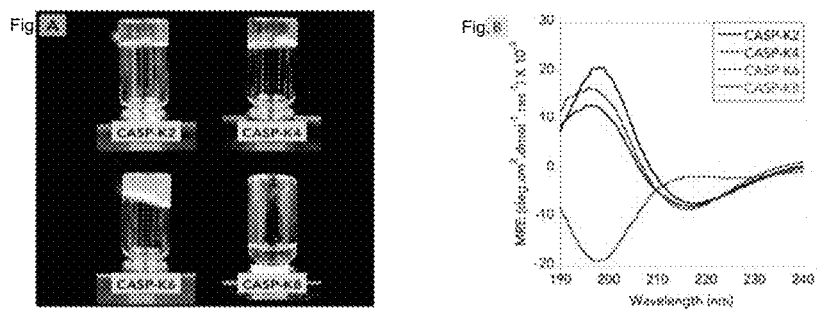
FIGS. 4A-4B are a photograph and graph showing material formulation and secondary structure of CASPs.
Figure 17:
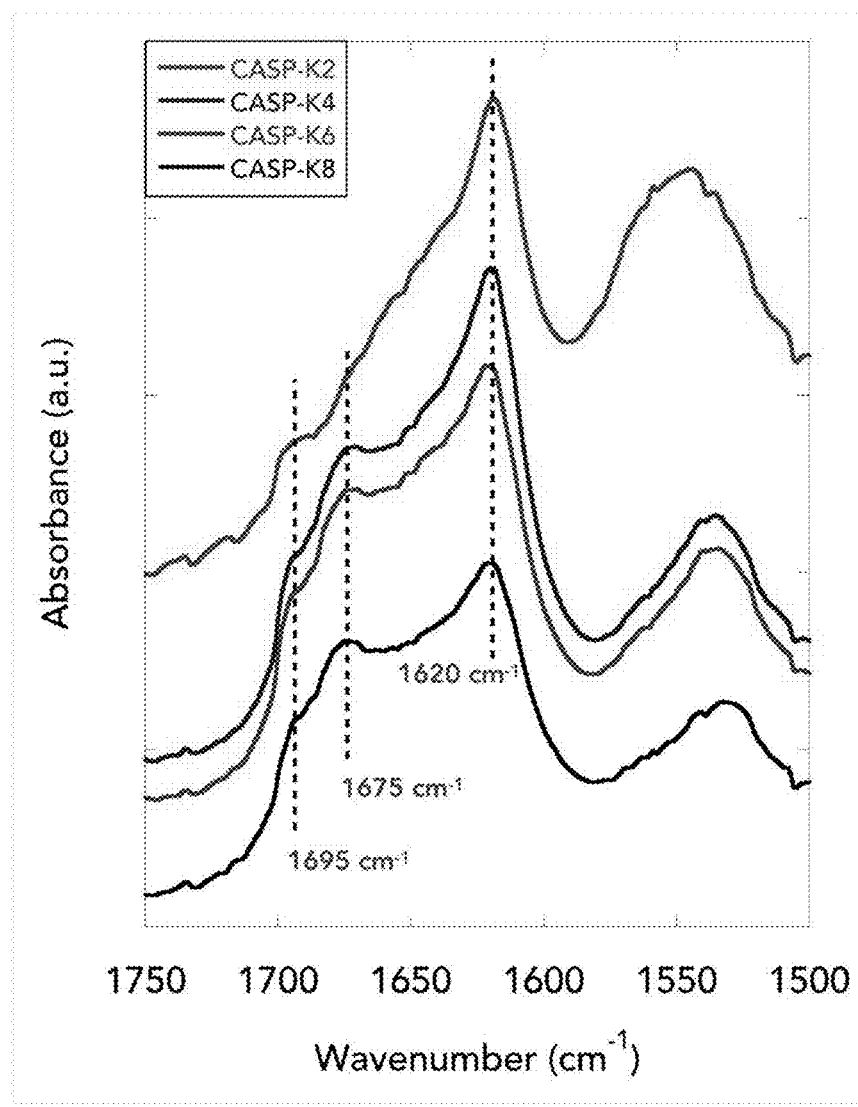
FIG. 17 is a FTIR spectra for CASPs (amide I region), the spectra have been offset on the y-axis for clarity, in dried film form, all of the CASPs show a characteristic amide-I peak for β-sheets (1620 cm$^{-1}$), however, the peak gets considerably broader as the charge of the peptide is increased (CASP-K2 to CASP-K8), suggesting contribution from a random-coil structure, note that the β-sheet propensity of CASP-K8 seems to be higher at a dense semi-dried state (the FTIR sample) than in a dilute solution (0.002% CD sample), a shoulder at 1695 cm$^{-1}$ is indicative of anti-parallel β-sheet secondary structure, the 1675 cm$^{-1}$ peak has been previously ascribed to lysine side chains.

However, under identical conditions, CASP-K8 remained in solution (FIG. 4A). The inability of CASP-K8 to form a hydrogel may be attributed to the extremely high charge density at its termini and the resultant inter-peptide repulsion. This interpretation is further supported by the secondary structure of the peptides as demonstrated by circular dichroism (CD) spectra (FIG. 1B, see FIG. 17 for infrared spectra). CASP-K2 through CASP-K6 formed β-sheets in accordance with FIG. 2. However, for CASP-K8, the repulsion among the terminal charged domains prevented the fibrillar association, leading to a random coil conformation and eliminating the peptide for consideration as an antibacterial hydrogel.

Hydrogel-forming peptides (CASP-K2 through CASP-K6) were characterized further using scanning electron microscopy (SEM) and atomic force microscopy (AFM) to determine the underlying nanostructures. All three peptides demonstrated nanofibrillar assembly. Representative SEM and AFM images of CASP-K6 nanofibers are shown at various resolutions in FIG. 5A-5D and also seen in FIGS. 6A-6C and FIGS. 7A-7D. The nanofibrous mesh is similar to previously described self-assembling peptide nanofibers used for tissue engineering applications, and anticipate that the current set of antibacterial peptides may potentially be integrated with such scaffolds.

Hydrogelation of the CASP system may be useful, among other things, for topical applications on infected wounds, similar to previous applications of self-assembling peptide hydrogels for rapid hemostasis and wound healing.

Figures 5A, 5B, 5C, 5D:
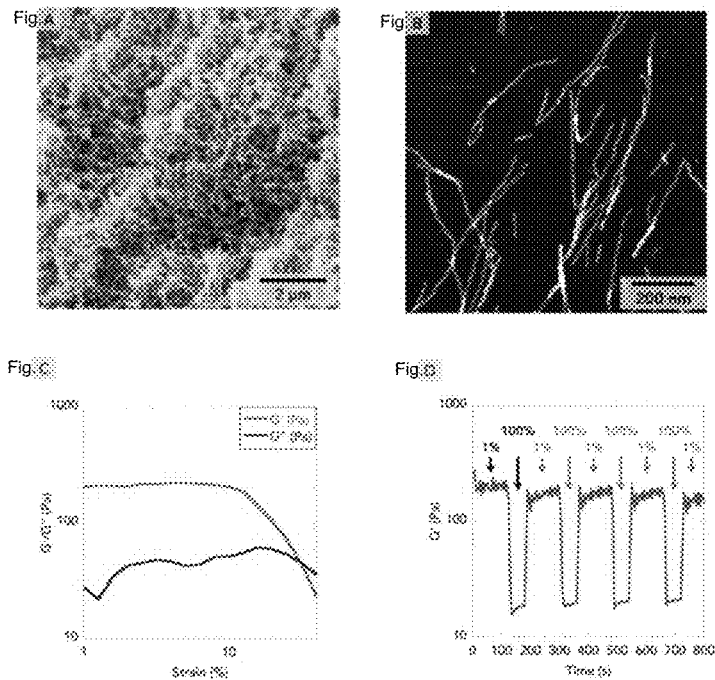
FIGS. 5A-5D are photomicrographs and graphs showing characterization of CASP-K6 hydrogel.
Figures 6A, 6B, 6C:
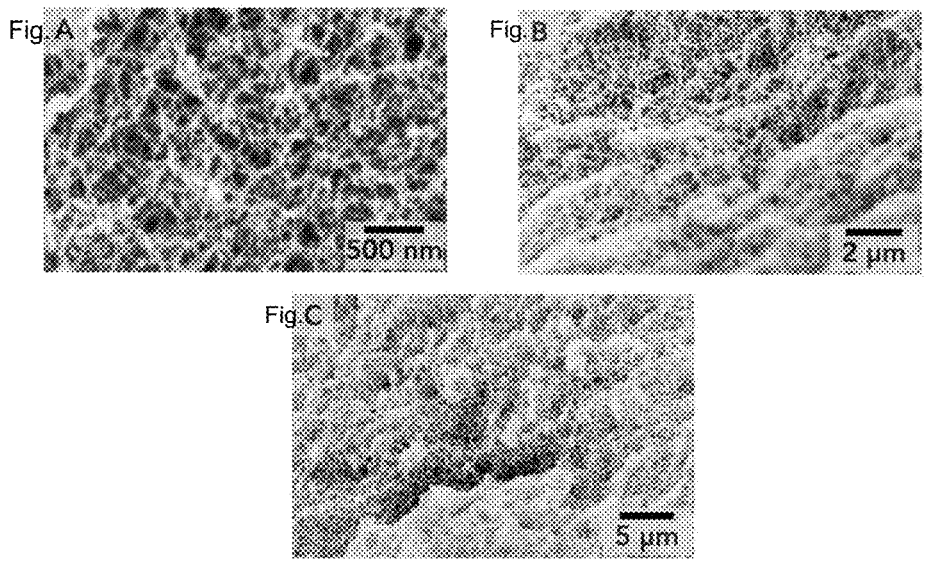
FIGS. 6A-6C are SEM images of CASP-K6 hydrogel at different resolutions (after critical-point drying and sputter-coating with gold/palladium), and the underlying mesh-like nanofibrous scaffold is revealed.
Figures 7A, 7B, 7C, 7D:
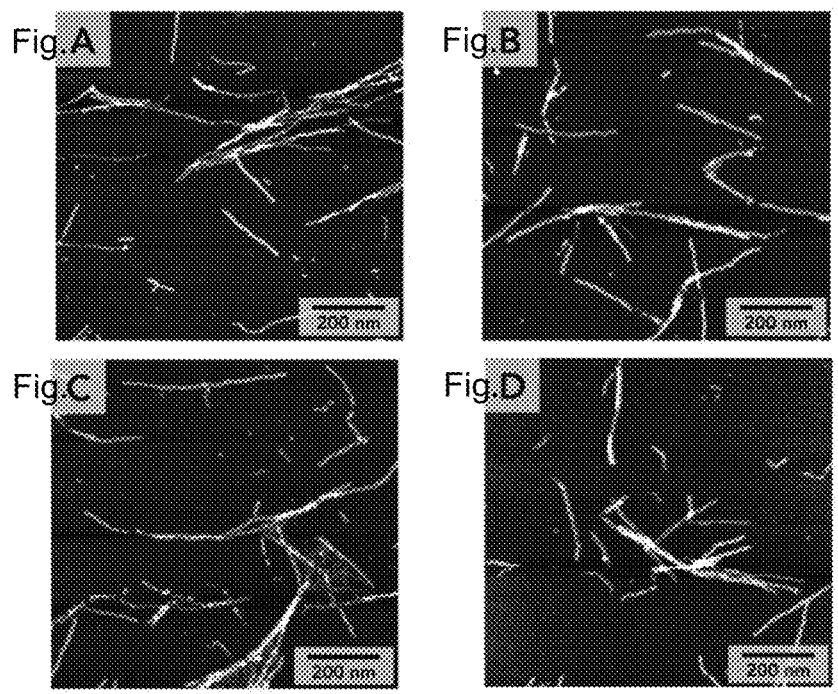
FIGS. 7A-7D are atomic force microscopy (AFM) images of CASP-K6 nanofibers, and individual nanofibers (~2 nm high and ~11 nm wide) observed.
Figure 8:
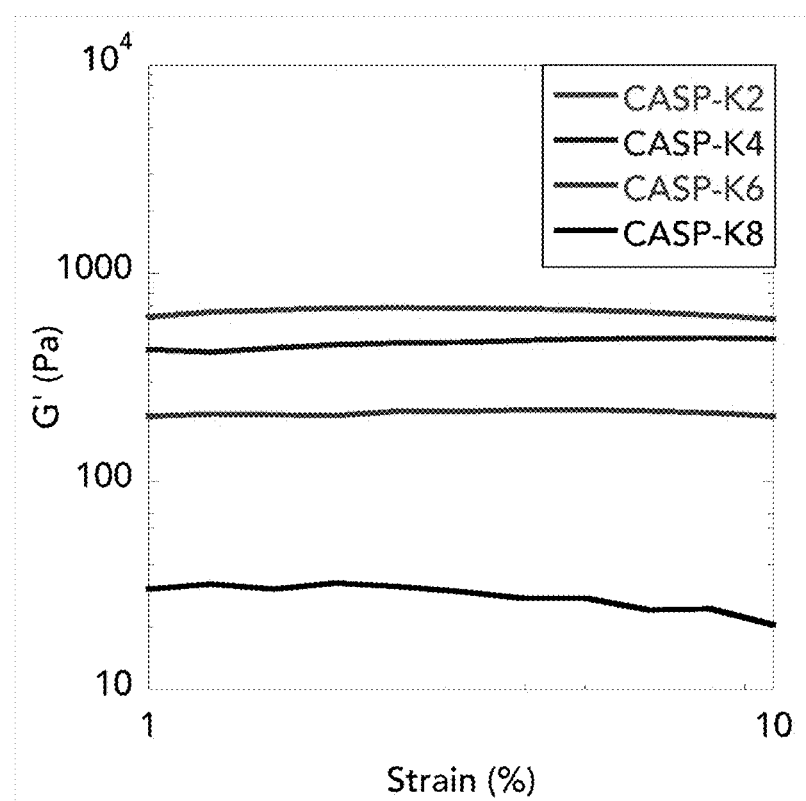
FIG. 8 is a graph showing comparison of storage modulus of CASP hydrogels/solutions (2% w/v) at low shear stress (1% to 10% strain), storage modulus (G') of the hydrogel drops rapidly as the terminal charge of the peptide increases, at 1% strain, the G' of the hydrogels/solutions are ~620 Pa (CASP-K2), ~430 Pa (CASP-K4), ~210 Pa (CASP-K6), and ~30 Pa (CASP-K8), the solutions with G' higher than 100 Pa are hydrogels.
Figures 9A, 9B, 9C, 9D, 9E:
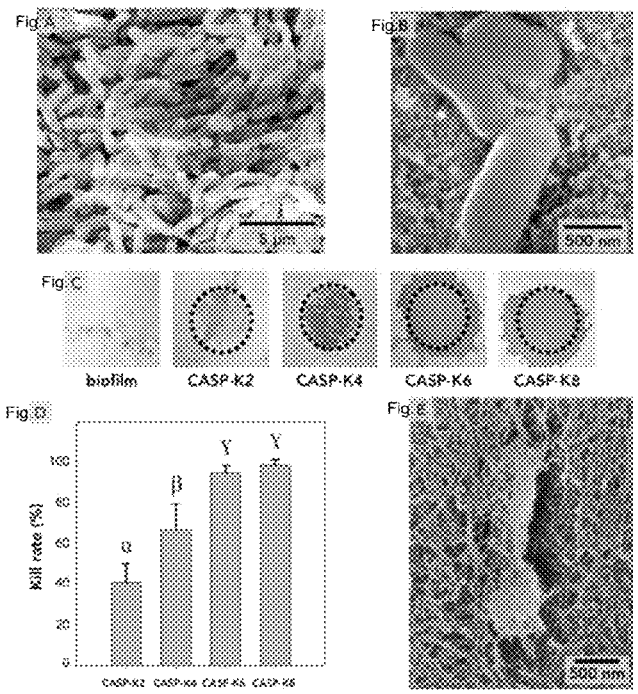
FIG. 9A-9E are illustrations of antibacterial activity of CASPs.
Figures 10A, 10B, 10C:
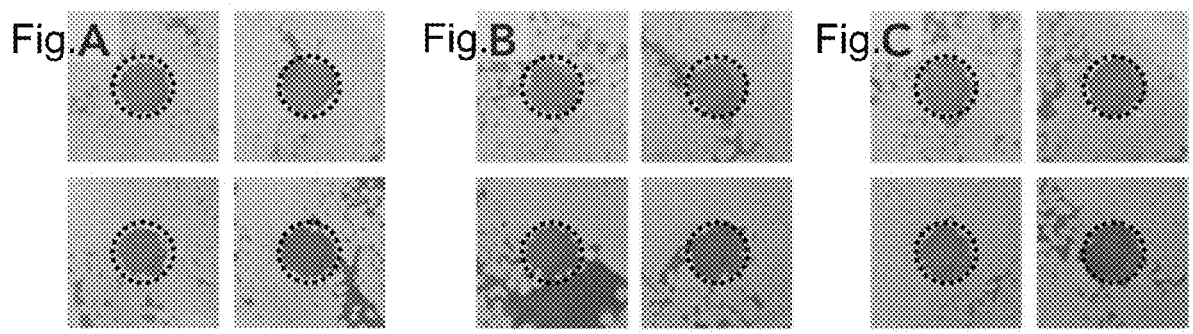
FIG. 10A-10C are photomicrographs showing images of the bacterial colonies exposed to the CASP-K6 hydrogel, where the hydrogel was injected on top of the bacterial colony inside the shown circled region.
Figure 11:
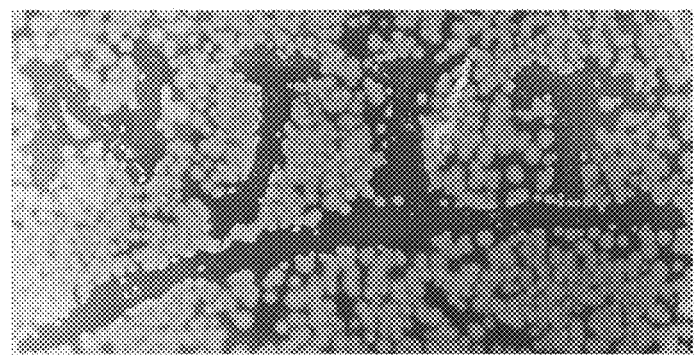
FIG. 11 is a photomicrograph showing a NJIT logo printed on a *P. aeruginosa* layer on agar using a CASP-K6 hydrogel to illustrate the localized efficacy of the discovered hydrogel.
Figures 12A, 12B:
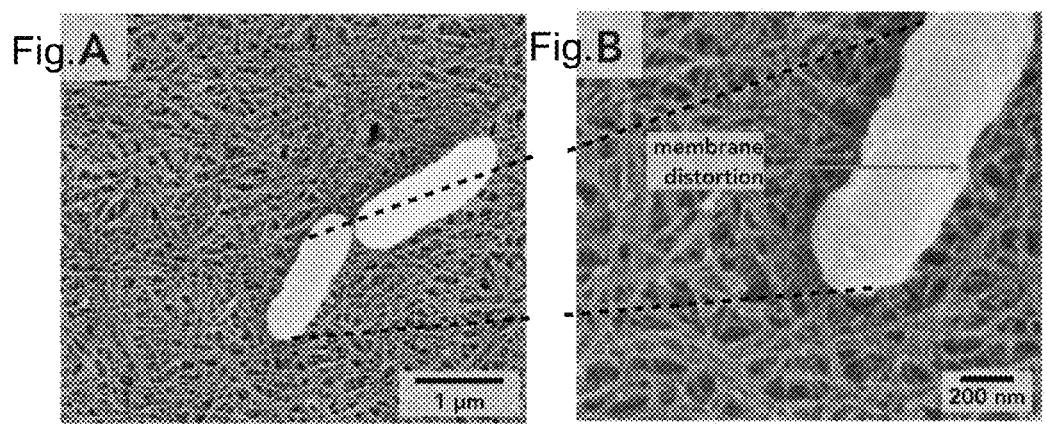
FIGS. 12A-12B are SEM images showing distortion of bacterial cell membranes on the cationic nanofibers of CASP-K6.
Figures 13A, 13B, 13C:
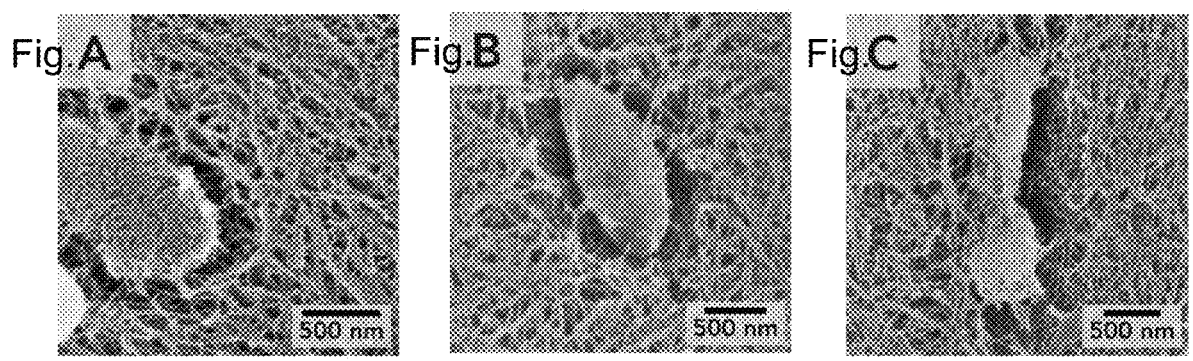
FIGS. 13A-13C are images showing bacterial cells entombed in the network of the cationic nanofibrous mesh of CASP-K6, in panel A and C, the membranes appear to be perforated or breached.
Figure 16A:
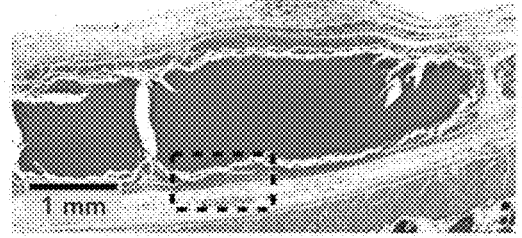
FIGS. 16A-16H are images showing subcutaneous implants of CASP-K6 persist in vivo and are clearly visible at (FIGS. 16A-D) day 1 and (FIGS. 16 E-H) day 3, cellular infiltration is observed on day 3 at the periphery of the hydrogel into the implant, where the cellular infiltration is most clearly visible in panels FIGS. 16F and 16H.
Figure 16B:
Figure 16C:
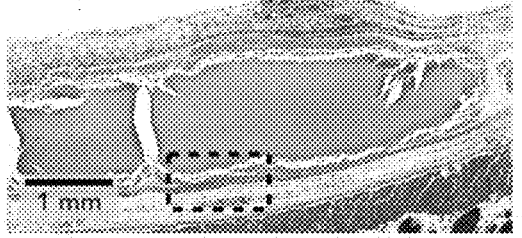
Figure 16D:
Figure 16E:
Figure 16F:
Figure 16G:
Figure 16H:

Comparable antibacterial peptides are often mixed with a gel base, such as hypromellose, to obtain a viscoelastic hydrogel formulation. The supramolecular design of the present peptides allow for the formation of an antibacterial hydrogel at physiological pH and ionic strength without the addition of a gel base as seen in FIG. 4A and FIG. 8. Rheometry suggests that the CASP-K6 hydrogel has a storage modulus of >200 Pa, comparable to previous self-assembled therapeutic peptide hydrogels. Fibrillar assembly of CASP-K6 is driven by non-covalent crosslinking—thus, the hydrogel can liquefy under high shear strains (>30%, FIG. 5C), as well as rapidly recover its viscoelasticity (G/G") when the force is removed (FIG. 5D). The shear-thinning and rapid recovery of the hydrogel can allow the gel to be syringe aspirated and injected into infection sites in vivo.

Colonies of the gram-negative bacteria *Pseudomonas aeruginosa* PAO1 were grown on agar and CASP solutions were applied to assess their colony-disruption ability (FIGS. 9A-9E). Cationic amphiphilic peptide nanofibers show noticeable bactericidal effect. This effect was correlated with the terminal charge on the cationic nanofibers (FIGS. 9C-9D), consistent with the hypothesis that a greater terminal charge facilitates the association of the peptide nanofibrils with the bacterial cell membrane. The effect of the antibacterial hydrogel was localized to an extent that were able to print our school logo (NJIT) on a bacterial film using CASP-K6 hydrogel as seen in FIGS. 10A-10C and FIG. 11.

However, as discussed before, the disrupted fibrillar assembly of CASP-K8 (FIGS. 4A-4B, FIG. 8) precludes its application as an antimicrobial hydrogel in a localized and controlled fashion. CASP-K6 had comparable antibacterial activity and formed a nanofibrous hydrogel (FIGS. 4A-4B, FIGS. 5A-5D). CASP-K6 nanofibers associated with bacterial cells, which led to membrane rupture as captured via SEM (FIG. 9E, FIGS. 12A-12B, FIGS. 13A-13C, and FIG. 14).

The CASP-K6 peptide shares its core antibacterial features (cationic nature, amphiphilicity) with natural antimicrobial peptides, such as LL-37. However, LL-37 is susceptible to enzymatic degradation in vivo within a time period of hours, limiting its therapeutic potential. In contrast, CASP-K6 persists in vivo (FIGS. 15A-15D, FIGS. 16A-16H), ensuring lack of prompt enzymatic degradation.

To test the in vivo persistence of the peptide, Wistar rats were subcutaneously injected with 200 μL CASP-K6 hydrogel (2% w/v). Because of the thixotropic nature of the hydrogel, it reconstituted post-injection in the subcutaneous pocket. At prescribed time intervals (1, 3, and 7 days), the rats were sacrificed and the dorsal skin covering the implant was removed for histological examination. Used was hematoxylin and eosin (H&E) FIGS. 15A-15B, and Masson's trichrome staining FIGS. 15C-15D) to analyze the tissue sections.

The subcutaneous implant showed little cellular infiltration and remained observable for at least 7 days (earlier time points shown in FIGS. 16A-16H). This lower degree of infiltration at 7 days was contrary to previous reports of softer hydrogels (lower G') having greater cellular infiltration than stiffer (higher G') hydrogels. When CASP-K6 is compared to CASP-K2 hydrogels, it is observed that the stiffer CASP-K2 hydrogels had relatively higher degrees of infiltration.

Figure 18A:
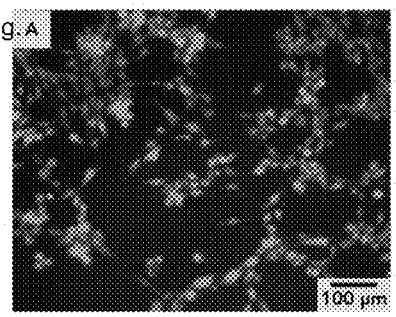
FIGS. 18A-18C are illustrating cytocompatibility of CASP-K6 with respect to fibroblasts, the peptide shares its core antibacterial features (natural amino acids, cationic nature, and amphiphilicity) with natural antimicrobial peptides, which have shown biocompatibility with mammalian cells, this may explain the low toxicity with respect to mammalian cells, such as 3T3 fibroblasts, this property may be important for application of the hydrogel, ensuring the lack of off-site toxicity in the host.
Figure 18B:
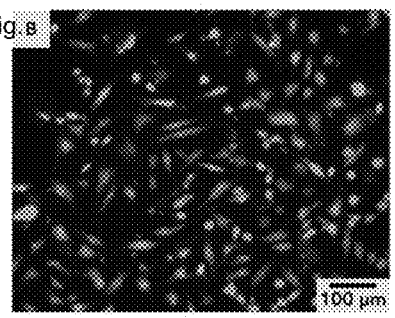
Figure 18C:
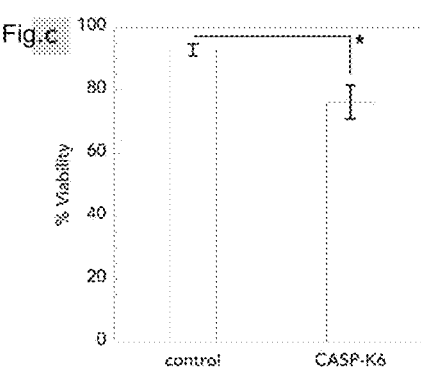

These results suggest that the higher charge density of CASP-K6 nanofibers may inhibit infiltration, potentially enabling prolonged persistence of the implant in situ despite having less robust self-assembly (see FIG. 8). Moreover, the implants did not induce any local/systemic toxicity or mortality in the rats. Coupled with an in vitro cytocompatibility assay (FIGS. 18A-18C), these results indicated preliminary safety of the hydrogel.

In summary, it is shown that CASP nanofibers can self-assemble into robust hydrogels and are potent disruptors of bacterial colonies. These hydrogels can be syringe aspirated and injected onto or into a target site. A self-assembling peptide, CASP-K6, that is optimized for both fibrillar self-assembly and antibacterial efficacy is found to be extremely useful in preventing the spread of bacterial contamination. Self-assembled nanostructures are shown to have higher antimicrobial efficacy compared to the corresponding unassembled peptide due to higher local density of functional bactericidal domains.

Building on this work, the next step is to test this platform against a range of multi-drug resistant bacterial biofilms in a dose-dependent manner and test the antibacterial efficacy changes in the presence of body fluids. In addition, it is within the scope of this invention to recognize possible routes of resistance development in bacteria in response to the peptide nanofibers as well as long-term sequelae of the treatment. The detailed mechanism by which these peptides disrupt the bacterial membrane may be investigated. Several membrane rupture mechanisms for natural AMPs as well as synthetic antibiotic peptides are possible.

It is anticipated that the CASP system of the present disclosure may be used in conjunction with other self-assembling peptide scaffolds to design multi-component tissue-engineering constructs. Such hybrid scaffolds may become useful tools in the arsenal for the repair and regeneration of tissues while minimizing infection-related failure. Establishment of this self-assembled nanofibrous platform may lead to clinical advances in pathogen-resistant biomaterials as well as injectable/topical antibacterial hydrogels.

Experimental Section

Peptide Synthesis and Preparation:

The series of CASPs were synthesized through solid-phase peptide synthesis using a Liberty Blue microwave peptide synthesizer (acetyl N-terminal and amide C-terminal protective groups). The reagents and starting materials were purchased from CEM Corporation and Fisher Scientific. Rink amide resin was used with 0.18 mmol/g loading. The peptides were purified by dialysis (against deionized water with 2000 Da molecular weight cut-off dialysis tubing). Then, the peptides were then lyophilized and identified with matrix-assisted laser desorption/ionization mass spectrometry (MALDI-MS) or electrospray ionization mass spectrometry (ESI-MS).

Peptide Characterization:

Scanning electron microscopy (SEM), atomic force microscopy (AFM), rheology, and Fourier-transform infrared spectroscopy (FTIR) methods have been described previously.

For SEM, hydrogel samples were processed by fixing in glutaraldehyde, dehydrating in ethanol dehydrated, and critical-point drying. The critical-point dried samples were then sputter-coated with gold/palladium and imaged with LEO 1530VP Field Emission Scanning Electron Microscope at a working distance of ~10 mm.

To conduct AFM analysis, the peptide hydrogel was diluted 10-fold in water (0.2%). The diluted solution was deposited on a freshly cleaved mica disc. Performed was a spin-coating on a purpose-built spin-coater. The coated mica disc was air dried for 30 minutes prior to imaging. Used was a PeakForce tapping (ScanAsyst) mode on a Bruker Dimension FastScan® AFM machine.

For rheology, 2% peptide hydrogel was transferred between a plate and a 4 mm parallel plate geometry with a gap of 350 μm, on a Malvern Kinexus Ultra+rheometer. Strain sweep (0.1-100% strain at 1 Hz) and shear recovery (1% strain at 1 Hz for 5 min, 100% strain at 1 Hz for 1 min, and 1% strain at 1 Hz for 5 min) were carried out. Shear recovery was repeated several times to demonstrate hydrogel resilience.

For FTIR, 2 μL of peptide hydrogels (2%) were pipetted onto an attenuated total reflectance (ATR) set-up and air-dried into a thin film. Infrared spectra between 400 cm$^{-1}$ and 4000 cm$^{-1}$ were collected, using a Spectrum 100 FTIR spectrometer (PerkinElmer). For clarity the relevant amide-I region is depicted in the STIR spectra below. For circular dichroism (CD), an Olis Rapid Scanning Monochromator (RSM) was used to measure the ellipticity of a 0.002% peptide solution from 190 nm to 240 nm in a 1 cm cuvette. The ellipticity (θ, measured in milidegrees) was converted to molar residual ellipticity (MRE) [θ] according to the formula: $[\theta]=(\theta \cdot m)/(10 \cdot c \cdot l \cdot n)$, [m=molecular weight of the peptide, c=concentration of the peptide solution in mg/mL, l=path length of the cuvette in cm, and n=no. of residues in the peptide sequence] (calculations described previously). Depending on the embodiment, a concentration of the CASP-K6 in aqueous solution resulting in aggregation or hydrogelation is 0.01 mg/ml-100 mg/ml.

Peptide Efficacy and Safety:

To test the efficacy of CASPs against bacterial colonies, *Pseudomonas aeruginosa* (PAO1) were cultured on agar plates and peptide hydrogels/solutions were placed on these bacteria cultures during the exponential growth phase to evaluate the antibacterial properties. The experiment to test antibacterial activity of the peptides was carried out over 4 days. On day 1, an agar plate was streaked with the bacteria using an inoculating loop. The streaked plate was then kept in an incubator to allow for bacterial growth overnight. Day 2 consisted of inoculating one colony of bacteria from the streaked plate into a glass tube filled with 5 mL of the Luria-Bertani (LB) broth. The tube is then set aside to allow for the colony to grow overnight in the LB broth. The following day the agar plates were labeled with the type of bacteria, concentration used, treatment being tested, and the date.

The areas of treatment on the plate were also shown with a circle to indicate where the treatment was applied as well as the amount applied. 100 μL of the bacterial suspension required for the experiment was added to an agar plate and spread evenly over the agar using a rotator tool. The plates were left to dry for about 30 seconds. Next, the desired amount of the peptide solution was applied to the labeled areas on the plate and kept in an incubator overnight. On Day 4, the inhibition zones were characterized by digital photography (n=4 for each CASP). For samples of the most promising candidate (CASP-K6), the plate was then treated with glutaraldehyde, critical point dried, and imaged by SEM.

For in vitro cytocompatibility tests, cultured were NIH 3T3 fibroblasts in DMEM supplemented with 10% FBS and 1× penicillin-streptomycin in T75 flasks. After the fibroblasts reached confluency, they were seeded in a 96-well plate at 2,500 cells/well. 0.002% CASP-K6 (n=6) and a control (media with sucrose and phosphate-buffered saline (PBS), n=6) were tested. For the former, the peptide was supplemented in the media, and for the control, 298 mM sucrose and PBS was supplemented to the media. The sucrose and PBS supplemented in the media control corresponded to the quantities required to formulate CASP-K6. Media was changed daily for 3 days and cytocompatibility was assessed on day 3 using a LIVE/DEAD viability/cytotoxicity kit (images were taken on a Nikon Eclipse Ti—S inverted fluorescent microscope). A NIH ImageJ was used to quantify cell viability.

For in vivo subcutaneous implantations, NJIT-Rutgers animal care facility was used. Injected was ~200 µL CASP-K6 hydrogels in the subcutaneous pocket (dorsal aspect) of female Wistar rats (~250 g, Charles River) (four implants (n=4) per rat). At the specified time points (1 day, 3 day, and 7 day), the animals were sacrificed and regions around the implant were excised, fixed, and processed. Hematoxylin and eosin (H&E) and Masson's trichrome staining was used for histologic analysis.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

---

What is claimed is:

1. An anti-bacterial hydrogel, comprising
a cationic amphiphilic self-assembled peptide (CASP-K6) comprising SEQ. ID. NO. 3, and
wherein, the CASP-K6 is a hydrogel with a self-assembled nanofiber platform for disrupting bacterial colonies in stationary biofilms.

2. The anti-bacterial hydrogel of claim 1, wherein the CASP-K6 intrinsically undergoes self-hydrogelation in aqueous solutions without addition of an exogenous gel base.

3. The anti-bacterial hydrogel of claim 2, wherein the hydrogel is topically applied or integrated into a wound bed directly, or integrated into medical coatings, grafts, devices, and prostheses for reducing risk of bacterial infection and related failure.

4. The anti-bacterial hydrogel of claim 1, wherein the peptide CASP-K6 inhibits growth of a bacterial biofilm.

5. The anti-bacterial hydrogel of claim 4, wherein the bacterial biofilm further includes a colony of gram-negative bacteria.

6. The anti-bacterial hydrogel of claim 1, wherein the peptide CASP-K6 forms an antibacterial hydrogel at a physiological pH and a physiological ionic strength without addition of a gel base including hypromellose to obtain a viscoelastic hydrogel formulation.

7. The anti-bacterial hydrogel of claim 1, wherein a concentration of the CASP-K6 in aqueous solution resulting in aggregation or hydrogelation is 0.01 mg/ml-100 mg/ml.

8. A method of applying an antibacterial hydrogel, comprising:
providing an effective amount of a set of cationic amphiphilic self-assembled peptides (CASP-K6) that employ high-charge density to disrupt bacterial membranes comprising SEQ. ID. NO. 3;
wherein, the CASP-K6 is a hydrogel with a self-assembled nanofiber platform for disrupting bacterial colonies in stationary biofilms; and
delivering an injectable dosage of the peptide CASP-K6.

9. The method of claim 8, wherein the delivering is through an injectable syringe, a topical application, or integration into a medical coating.

10. The method of claim 9, wherein the medical coating is on a graft, a medical device, or prosthesis for reducing risk of a bacterial infection and a related failure.

11. The method of claim 8, wherein the peptide CASP-K6 is injectable, persists in vivo, and sustains a localized efficacy for a prolonged period.

12. The method of claim 8, further includes treating a localized infection to prevent bacterial growth or infection.

13. The method of claim 8, further includes using the peptide CASP-K6 in conjugation with another biomaterial.

14. An anti-bacterial hydrogel, comprising
a cationic amphiphilic self-assembled peptide (CASP-K6) comprising SEQ. ID. NO. 3;
wherein, the CASP-K6 is a hydrogel with a self-assembled nanofiber platform for disrupting bacterial colonies in stationary biofilms; and
wherein a hydrogelation of the peptide CASP-K6 occurs in vivo under a physiological pH without addition of a gel base to form the hydrogel and wherein the gel has a storage modulus of greater than 100 Pascals (Pa).

15. The anti-bacterial hydrogel of claim 14, wherein the hydrogelation is used for a topical application on an infected wound for rapid hemostasis and wound healing.

16. The anti-bacterial hydrogel of claim 5, wherein the colony of gram-negative bacteria is *Pseudomonas aeruginosa* PAO1.

17. The anti-bacterial hydrogel of claim 6, wherein the hydrogel has a storage modulus greater than 100 Pascals (Pa).

* * * * *

SEQUENCE LISTING

```
<160> NUMBER OF SEQ ID NOS: 4

<210> SEQ ID NO 1
<211> LENGTH: 16
<212> TYPE: PRT
<213> ORGANISM: Artificial Sequence
<220> FEATURE:
<223> OTHER INFORMATION: CASP-K2

<400> SEQUENCE: 1

Lys Lys Ser Leu Ser Leu Ser Leu Ser Leu Ser Leu Ser Leu Lys Lys
1               5                   10                  15

<210> SEQ ID NO 2
<211> LENGTH: 20
<212> TYPE: PRT
<213> ORGANISM: Artificial Sequence
<220> FEATURE:
<223> OTHER INFORMATION: CASP-K4

<400> SEQUENCE: 2

Lys Lys Lys Lys Ser Leu Ser Leu Ser Leu Ser Leu Ser Leu Ser Leu
1               5                   10                  15

Lys Lys Lys Lys
            20

<210> SEQ ID NO 3
<211> LENGTH: 24
<212> TYPE: PRT
<213> ORGANISM: Artificial Sequence
<220> FEATURE:
<223> OTHER INFORMATION: CASP-K6

<400> SEQUENCE: 3

Lys Lys Lys Lys Lys Lys Ser Leu Ser Leu Ser Leu Ser Leu Ser Leu
1               5                   10                  15

Ser Leu Lys Lys Lys Lys Lys Lys
            20

<210> SEQ ID NO 4
<211> LENGTH: 28
<212> TYPE: PRT
<213> ORGANISM: Artificial Sequence
<220> FEATURE:
<223> OTHER INFORMATION: CASP-K8

<400> SEQUENCE: 4

Lys Lys Lys Lys Lys Lys Lys Lys Ser Leu Ser Leu Ser Leu Ser Leu
1               5                   10                  15

Ser Leu Ser Leu Lys Lys Lys Lys Lys Lys Lys Lys
            20                  25
```